US008882348B2

(12) United States Patent
Herrmann et al.

(10) Patent No.: US 8,882,348 B2
(45) Date of Patent: Nov. 11, 2014

(54) C-ARM SUPPORT DEVICE FOR A MOBILE C-ARM X-RAY MACHINE

(75) Inventors: Norbert Herrmann, Ebnath (DE); Andreas Limmer, Fuerth (DE)

(73) Assignee: Siemens Aktiengesellschaft, München (DE)

( * ) Notice: Subject to any disclaimer, the term of this patent is extended or adjusted under 35 U.S.C. 154(b) by 329 days.

(21) Appl. No.: 13/403,757

(22) Filed: Feb. 23, 2012

(65) Prior Publication Data
US 2012/0219122 A1 Aug. 30, 2012

(30) Foreign Application Priority Data

Feb. 24, 2011 (DE) .......................... 10 2011 004 667

(51) Int. Cl.
*H05G 1/02* (2006.01)
*A61B 6/00* (2006.01)

(52) U.S. Cl.
CPC .................................... *A61B 6/4405* (2013.01)
USPC ........................................................ 378/198

(58) Field of Classification Search
USPC ........................................................ 378/198
See application file for complete search history.

(56) References Cited

U.S. PATENT DOCUMENTS

| 5,627,873 | A  | * | 5/1997  | Hanover et al. ............... 378/198 |
| 7,766,548 | B2 | * | 8/2010  | Dehler et al. ................. 378/198 |
| 2009/0296892 | A1 | | 12/2009 | Fadler et al. |
| 2011/0058656 | A1 | * | 3/2011  | Hartwich et al. ............. 378/198 |

FOREIGN PATENT DOCUMENTS

| DE | 8521246 U1 | 2/1986 |
| DE | 39 00 312 A1 | 2/1990 |
| DE | 101 11 798 A1 | 10/2002 |
| DE | 10 2008 026 622 A1 | 12/2009 |

OTHER PUBLICATIONS

Translation for DE 8521246 U1 published on Feb. 20, 1986.*
German Office Action dated Nov. 8, 2011 for corresponding German Patent Application No. DE 10 2011 004 667.4 with English translation.

* cited by examiner

*Primary Examiner* — Glen Kao
(74) *Attorney, Agent, or Firm* — Lempia Summerfield Katz LLC

(57) ABSTRACT

The present embodiments relate to a wheeled C-arm support device for a mobile C-arm X-ray machine and an associated method for swiveling the C-arm support device. The C-arm support device includes two steerable front wheels, two freely movable rear wheels and a steering unit that may steer the two steerable front wheels simultaneously inward by the same angle. A line of intersection of surfaces formed by outer sides of the two steerable front wheels form an imaginary swivel axis of the C-arm support device.

10 Claims, 2 Drawing Sheets

C-ARM SUPPORT DEVICE FOR A MOBILE C-ARM X-RAY MACHINE

This application claims the benefit of DE 10 2011 004 667.4, filed on Feb. 24, 2011.

BACKGROUND

The present embodiments relate to a C-arm support device and a method for swiveling a C-arm support device using steerable front wheels.

Mobile X-ray machines with C-arms may include a wheel- or roller-mounted support device (chassis), to which a C-arm including an X-ray source and an X-ray detector is mounted for diagnostic imaging. FIG. 1 shows a perspective view of a mobile C-arm X-ray machine, as disclosed, for example, in DE 10 2008 026 622 A1.

FIG. 1 shows an X-ray C-arm 1 disposed on a support device 2 with rollers 6. The X-ray C-arm 1 and the support device 2 are interconnected via a C-arm retaining module 5. Mounted at respective ends of the X-ray C-arm 1 are an X-ray emitter 3 and an X-ray detector 4. With the aid of the X-ray emitter 3, a patient lying on an examination table, for example, may be irradiated with X-rays that are captured by the X-ray detector 4. The X-ray C-arm 1 connected to the C-arm retaining module 5 may be displaced horizontally.

In order to achieve greater freedom of movement for examinations, the X-ray C-arm may be pivoted about one or more vertical axes of rotation, thereby enabling a region of interest to be examined without having to move the patient. DE 10 111 798 A1 shows such an arrangement. The rotation about the rotational axis is braked in order to avoid unintentional torsion of the C-arm. During the rotation, the C-arm and a horizontal unit are rotated. Stability is an issue. This is achieved by additional balancing weights or a large wheelbase. In addition, the rotational movement is limited in order to prevent the machine from tipping over.

SUMMARY AND DESCRIPTION

The present embodiments may obviate one or more of the drawbacks or limitations in the related art. For example, a C-arm support device for a mobile C-arm X-ray machine that is capable of being swiveled is provided.

In DE 85 21 246 U1, a portable X-ray diagnostic device is disclosed. The device may be displaced laterally by turning front and rear wheels sideways.

DE 39 00 312 A1 discloses a chassis for an X-ray device. Rear wheels may be steered in opposite directions using a steering device so that the X-ray device swivels about an axis at an intersection point of wheel axes of the rear wheels.

In one embodiment, a wheeled C-arm support device for a mobile C-arm X-ray machine includes two steerable front wheels and two freely movable rear wheels. A steering unit steers the two front wheels simultaneously inward at the same angle. A line of intersection of surfaces formed by outer sides of the front wheels constitutes a swivel axis of the C-arm support device. In contrast to a normal steering movement, in which the front wheels are always parallel to one another, the front wheels are displaced in opposite directions to one another. The present embodiments offer the advantage that neither an axle nor a brake are required for a swiveling movement, thereby saving costs and increasing the stability of the support device, as the swivel is produced by the wheels. The support device may also be made lighter, as no additional weights are required. The swivel may also be executed without rotational limiting.

In one embodiment, the front wheels are installed in a front region of the support device, and the rear wheels are installed in a rear half of the support device, on an underside of the support device.

In another embodiment, the rear wheels are each pivoted about a vertical axis. In the case of a rotational movement about the swivel axis, the rear wheels may be set in a swivel direction.

In one embodiment, a mobile C-arm X-ray machine having a C-arm support device is provided.

In one embodiment, a method for swiveling a C-arm support device with two front wheels for a mobile C-arm X-ray machine is provided. The two front wheels of the support device are simultaneously steered inward at the same angle so that an imaginary swivel axis (e.g., a swivel axis) of the C-arm support is formed by the line of intersection of the surfaces formed by the outer sides of the front wheels.

In one embodiment of the method, the C-arm support device is swiveled about the swivel axis.

In another embodiment, the front wheels are steered inward from a parallel position using a steering device.

In addition, during rotation about the swivel axis, two rear wheels of the support device are rotated in the swivel direction.

DETAILED DESCRIPTION OF THE DRAWINGS

Figure 1:
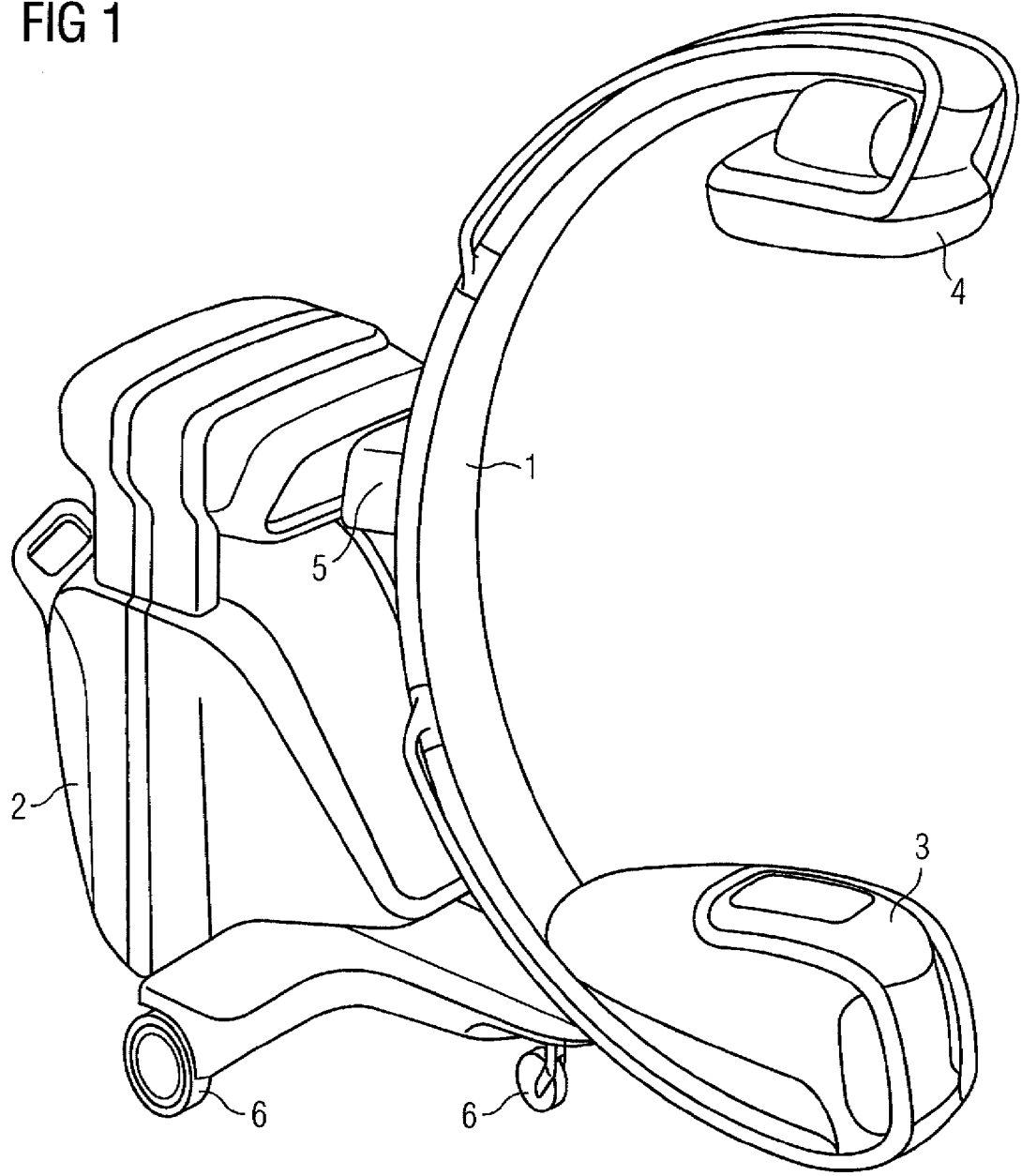
FIG. 1 shows a mobile C-arm X-ray machine according to the prior art.
Figure 2:
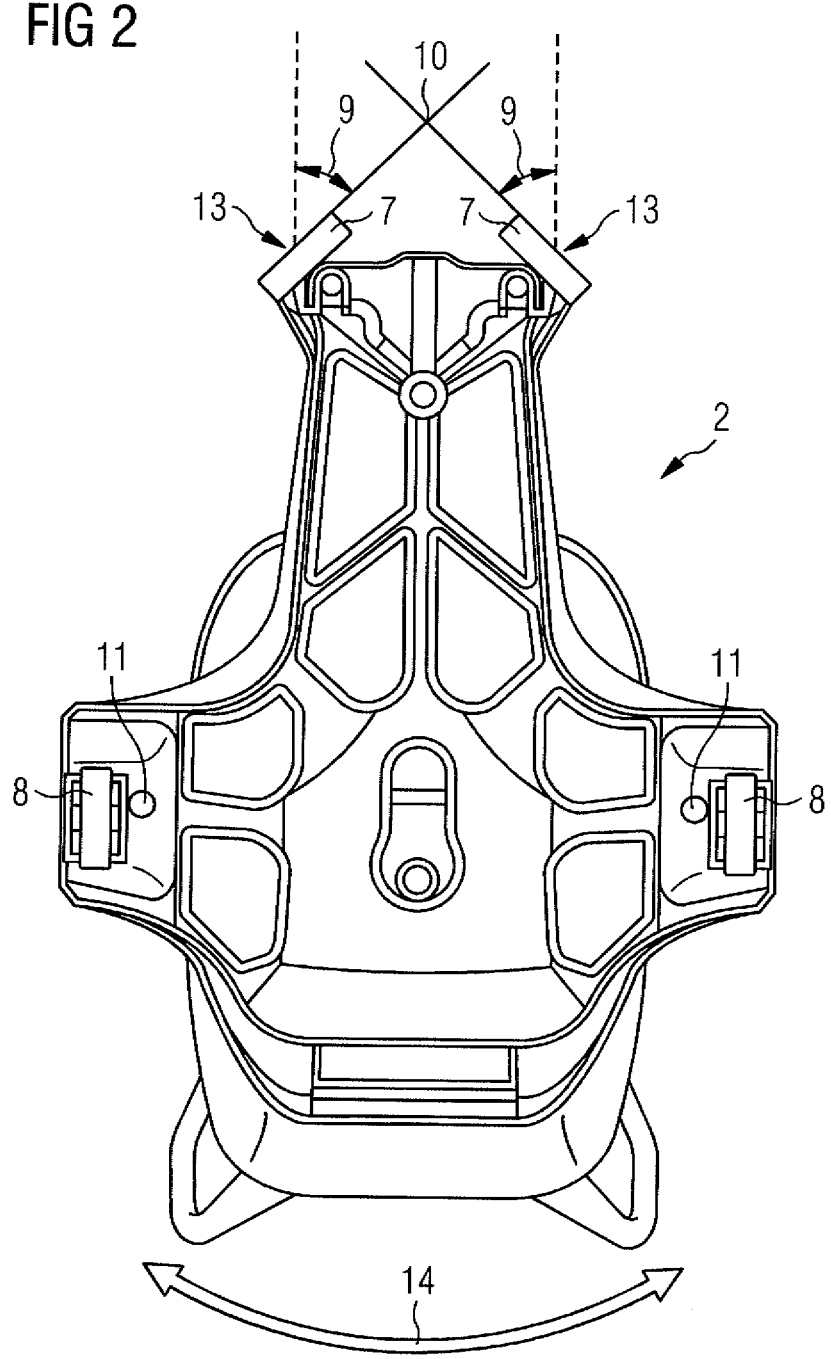
FIG. 2 shows a view from below of one embodiment of a C-arm support device with steerable front wheels.

FIG. 2 shows the view from below of a C-arm support device 2 (e.g., a support device) for a mobile C-arm X-ray machine. Visible in a front region of the support device 2 are two steerable front wheels 7 and two freely movable rear wheels 8 in a central region of the support device 2. Using a steering unit 12 including a steering linkage, the two steerable front wheels 7 may be simultaneously moved parallel to one another to displace the support device 2.

In one embodiment, the two front wheels 2 may also be steered in opposite directions to one another from a parallel position to a position angled inward to one another by a steer angle 9. Surfaces spanned by outer sides 13 of the front wheels 2 form a line of intersection that forms a swivel axis 10 of the support device 2. The support device 2 may be swiveled about the swivel axis 10 by moving the support device 2 in a direction of the arrow 14. The two rear wheels 8 are set in the swivel direction.

In one embodiment, the support device 2 may be used for a mobile C-arm X-ray machine, where a C-arm with an X-ray source and a diametrically opposed X-ray detector is movably mounted on the support device 2.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A wheeled C-arm support device for a mobile C-arm X-ray machine, the wheeled C-arm support device comprising:

two steerable front wheels;

two freely movable rear wheels; and a steering unit operable to steer the two steerable front wheels simultaneously inward at the same angle, a line of intersection of surfaces formed by outer sides of the two steerable front wheels forming a swivel axis of the wheeled C-arm support device, about which the wheeled C-arm support device swivels, wherein each of the two freely movable rear wheels is pivotable about a corresponding first axis and is settable in a swivel direction, such that the freely movable rear wheel is operable to rotate about a corresponding second axis while the wheeled C-arm support device is swiveled about the swivel axis.

2. The C-arm support device as claimed in claim 1, wherein the two steerable front wheels are disposed in a front region of the wheeled C-arm support device, and wherein each of the two freely movable rear wheels is disposed in a rear half of the wheeled C-arm support device, on an underside of the wheeled C-arm support device.

3. The C-arm support device as claimed in claim 2, wherein each of the two freely movable rear wheels is pivoted about a corresponding vertical axis.

4. The C-arm support device as claimed in claim 1, wherein each of the two freely movable rear wheels is pivoted about a corresponding vertical axis.

5. A mobile C-arm X-ray machine comprising:

a wheeled C-arm support device comprising:

two steerable front wheels;

at least one freely movable rear wheel; and a steering unit operable to steer the two steerable front wheels simultaneously inward at the same angle, a line of intersection of surfaces formed by outer sides of the two steerable front wheels forming a swivel axis of the wheeled C-arm support device, about which the wheeled C-arm support device swivels, wherein each freely movable rear wheel of the at least one freely movable rear wheel is pivotable about a corresponding first axis and is settable in a swivel direction, such that the at least one freely movable rear wheel is operable to rotate about a corresponding second axis while the wheeled C-arm support device is swiveled about the swivel axis.

6. A method for swiveling a C-arm support device for a mobile C-arm X-ray machine, the C-arm support device comprising two front wheels and a freely movable rear wheel, the method comprising:

steering the two front wheels of the C-arm support device simultaneously inward at the same angle, so that a swivel axis of the C-arm support device is formed by a line of intersection of surfaces formed by outer sides of the two front wheels; and pivoting the freely movable rear wheel about a first axis and setting the freely movable rear wheel in a swivel direction, such that the freely movable rear wheel is operable to rotate about a second axis while the C-arm support device is swiveled about the swivel axis.

7. The method as claimed in claim 6, wherein the two front wheels are steered inward from a parallel position using a steering unit.

8. The method as claimed in claim 7, wherein the freely movable rear wheel is a first freely movable rear wheel, and wherein, during swiveling about the swivel axis, the first freely movable rear wheel and a second freely movable rear wheel of the C-arm support device are rotated in a swivel direction.

9. The method as claimed in claim 6, wherein the freely movable rear wheel is a first freely movable rear wheel, and wherein, during swiveling about the swivel axis, the first freely movable rear wheel and a second freely movable rear wheel of the C-arm support device are rotated in a swivel direction.

10. The method as claimed in claim 9, wherein, during rotation about the swivel axis, the first freely movable rear wheel and the second freely movable rear wheel of the C-arm support device are rotated in the swivel direction.

\* \* \* \* \*